US00PP28627P3

(12) United States Plant Patent
Jackson et al.

(10) Patent No.: US PP28,627 P3
(45) Date of Patent: Nov. 14, 2017

(54) ***CERCIS* PLANT NAMED 'JN16'**

(50) Latin Name: *Cercis canadensis*
Varietal Denomination: JN16

(71) Applicants: Ray Jackson, Belvidere, TN (US); Cindy Jackson, Belvidere, TN (US)

(72) Inventors: Ray Jackson, Belvidere, TN (US); Cindy Jackson, Belvidere, TN (US)

( * ) Notice: Subject to any disclaimer, the term of this patent is extended or adjusted under 35 U.S.C. 154(b) by 78 days.

(21) Appl. No.: 14/998,740

(22) Filed: Feb. 9, 2016

(65) Prior Publication Data

US 2017/0231137 P1 Aug. 10, 2017

(51) Int. Cl.
*A01H 5/00* (2006.01)

(52) U.S. Cl.
USPC ..... Plt./216

(58) Field of Classification Search
USPC ..... Plt./216
See application file for complete search history.

(56) References Cited

U.S. PATENT DOCUMENTS

PP2,556 P * 9/1965 Keel et al. ..... Plt./216

OTHER PUBLICATIONS

Wener et al. 'Ruby Falls' and 'Merlot' Redbuds, HortScience 45(1):146-147, 2010.*

* cited by examiner

*Primary Examiner* — June Hwu
(74) *Attorney, Agent, or Firm* — C. A. Whealy

(57) ABSTRACT

A new and distinct cultivar of *Cercis* plant named 'JN16', characterized by its compact plant habit with relatively short internodes; deep purple-colored leaves; good garden performance with good leaf color retention during the summer.

1 Drawing Sheet

Botanical designation: *Cercis canadensis*.
Cultivar denomination: 'JN16'.

BACKGROUND OF THE INVENTION

The present invention relates to a new and distinct *Cercis* plant, botanically known as *Cercis canadensis*, commercially referred to as Eastern Redbud and hereinafter referred to by the name 'JN16'.

The new *Cercis* plant is a product of a planned breeding program conducted by the Inventors in Belvidere, Tenn. The objective of the breeding program was to develop new *Cercis* plants with purple-colored leaves that retain their color throughout the summer.

The new *Cercis* plant originated from a cross-pollination in May, 2012 in Belvidere, Tenn. of *Cercis canadensis* 'Ruby Falls', disclosed in U.S. Plant Pat. No. 22,097, as the female, or seed, parent with *Cercis canadensis* 'JN2', disclosed in U.S. Plant Pat. No. 21,451, as the male, or pollen, parent. The new *Cercis* plant was discovered and selected by the Inventors as a single plant within the progeny of the stated cross-pollination in a controlled nursery environment in Belvidere, Tenn. in May, 2013.

Asexual reproduction of the new *Cercis* plant by chip budding onto proprietary seedling *Cercis* rootstock in a controlled environment in Belvidere, Tenn. since August, 2013 has shown that the unique features of this new *Cercis* plant are stable and reproduced true to type in successive generations.

SUMMARY OF THE INVENTION

Plants of the new *Cercis* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'JN16'. These characteristics in combination distinguish 'JN16' as a new and distinct *Cercis* plant:

1. Compact plant habit with relatively short internodes.
2. Deep purple-colored leaves.
3. Good garden performance with good leaf color retention during the summer.

Plants of the new *Cercis* can be compared to plants of the female parent, 'Ruby Falls'. Plants of the new *Cercis* differ from plants of 'Ruby Falls' in the following characteristics:

1. Plants of the new *Cercis* are more compact than and not as pendulous as plants of 'Ruby Falls'.
2. Leaves of plants of the new *Cercis* maintain their deep purple color during the summer whereas leaves of plants of 'Ruby Falls' fade to a dull green color during the summer.

Plants of the new *Cercis* can be compared to plants of the male parent, 'JN2'. Plants of the new *Cercis* differ from plants of 'JN2' in the following characteristics:

1. Plants of the new *Cercis* are more compact than plants of 'JN2'.
2. Leaves of plants of the new *Cercis* maintain their deep purple color during the summer whereas leaves of plants of 'JN2' fade to a pale green color during the summer.

Plants of the new *Cercis* can be compared to plants of *Cercis canadensis* 'Forest Pansy', not patented. In side-by-side comparisons, plants of the new *Cercis* differed primarily from plants of 'Forest Pansy' in the following characteristics:

1. Plants of the new *Cercis* were more compact, had shorter internodes and were denser than plants of 'Forest Pansy'.
2. Plants of the new *Cercis* and 'Forest Pansy' differed in leaf color as plants of 'Forest Pansy' had lighter purple-colored leaves.
3. Leaves of plants of the new *Cercis* maintain their deep purple color during the summer whereas leaves of plants of 'Forest Pansy' are lighter purple in color during the summer.

Plants of the new *Cercis* can also be compared to plants of *Cercis canadensis* 'JN7', disclosed in U.S. Plant Pat. No. 25,701. In side-by-side comparisons, plants of the new *Cercis* differed primarily from plants of 'JN7' in the following characteristics:

1. Plants of the new *Cercis* were more compact than and not as upright as than plants of 'JN7'.
2. Plants of the new *Cercis* and 'JN7' differed in leaf color as plants of 'JN7' had green-colored leaves.
3. Leaves of plants of the new *Cercis* were glossier than plants of 'JN7'.

BRIEF DESCRIPTION OF THE PHOTOGRAPH

The accompanying colored photograph illustrates the overall appearance of the new *Cercis* plant showing the colors as true as it is reasonably possible to obtain in colored reproductions of this type. Colors in the photograph may differ slightly from the color values cited in the detailed botanical description which accurately describe the colors of the new *Cercis* plant.

The photograph is a side perspective view of a typical tree of 'JN16'.

DETAILED BOTANICAL DESCRIPTION

The aforementioned photograph and following observations, measurements and values describe trees grown during the spring, summer and autumn in 15-gallon containers in an outdoor nursery in Belvidere, Tenn. and Park Hill, Okla. and under cultural practices typical of commercial *Cercis* production. During the production of the plants, day temperatures ranged from 9.3° C. to 30.6° C. and night temperatures ranged from −1.9° C. to 18.8° C. Plants were four years old when the photograph and description were taken. In the description, color references are made to The Royal Horticultural Society Colour Chart, 2001 Edition, except where general terms of ordinary dictionary significance are used.

Botanical classification: *Cercis canadensis* 'JN16'.

Parentage:

*Female, or seed, parent.*—*Cercis canadensis* 'Ruby Falls', disclosed in U.S. Plant Pat. No. 22,097.

*Male, or pollen, parent.*—*Cercis canadensis* 'JN2', disclosed in U.S. Plant Pat. No. 21,451.

Propagation:

*Type.*—By chip budding onto proprietary seedling *Cercis* rootstock.

*Root description.*—Medium in thickness, fibrous; white in color.

*Rooting habit.*—Moderately freely branching; medium density.

Plant description:

*Plant and growth habit.*—Deciduous tree; compact plant habit; overall shape, broad oval; moderately vigorous growth habit; moderate growth rate.

*Branching habit.*—Freely branching habit with about 11 to 15 primary branches each with about 8 to 11 secondary branches.

*Plant height.*—About 1.9 meters.

*Plant diameter* (*area of spread*).—About 1.5 meters.

Lateral branch description:

*Length.*—Variable depending on position on the tree, average, about 70 cm.

*Diameter.*—About 8 mm.

*Internode length.*—About 4.4 cm.

*Aspect.*—Moderately upswept, about 45° from vertical.

*Strength.*—Moderately strong, firm.

*Texture and luster.*—Smooth, glabrous; semi-glossy.

*Color.*—Developing, close to 202A; at the internodes, close to N200A; developed, close to N200A.

Leaf description:

*Arrangement.*—Alternate, single.

*Length.*—About 14.9 cm.

*Width.*—About 13.8 cm.

*Shape.*—Reniform.

*Apex.*—Acute.

*Base.*—Cordate.

*Margin.*—Entire.

*Texture and luster, upper surface.*—Smooth, glabrous; glossy.

*Texture and luster, lower surface.*—Smooth, glabrous; matte.

*Venation pattern.*—Palmate.

*Color.*—Developing leaves, upper surface: Close to N186A. Developing leaves, lower surface: Close to N79B. Fully expanded leaves, upper surface: Close to N77A; venation, close to 132A. Fully expanded leaves, lower surface: Close to 138B and 59C; venation, close to 59A. Autumn leaf color, upper surface: Close to 151C. Autumn leaf color, lower surface: Close to 144C tinged with close to 161B.

*Petioles.*—Length: About 4.4 cm. Diameter: About 2 mm. Strength: Moderately strong. Texture and luster, upper and lower surfaces: Smooth, glabrous; semi-glossy. Color, upper surface: Close to 202A. Color, lower surface: Close to 187B.

Flower description:

*Flower arrangement and flowering habit.*—Single papilionaceous flowers arranged in terminal and axillary racemes with about seven flowers per raceme; freely flowering habit with about 8,000 flowers developing during the flowering season; flowers face mostly upright.

*Natural flowering season.*—Plants of the new *Cercis* flower in the mid-spring in Oklahoma; flowers last about ten days on the plant; flowers not persistent.

*Fragrance.*—None detected.

*Inflorescence diameter.*—About 1.2 cm.

*Inflorescence height.*—About 2.3 cm.

*Flower diameter.*—About 3 mm.

*Flower height.*—About 6 mm.

*Flower depth.*—About 1.5 mm.

*Flower buds.*—Length: About 1.5 mm. Diameter: About 1 mm. Shape: Ovoid. Texture and luster: Smooth, glabrous; matte. Color: Close to 202A.

*Petals*.—Arrangement: Typically five petals in a single whorl with upper three petals forming a banner (or standard) petal and lower petals forming a keel. Length, banner: About 6 mm. Length, keel: About 2.5 mm. Width, banner: About 2 mm. Width, keel: About 1 mm. Shape, all petals: Roughly ovoid. Apex, all petals: Rounded. Base, all petals: Rounded. Margin, all petals: Entire. Texture and luster, all petals: Smooth, glabrous; matte. Color, all petals: When opening, upper and lower surfaces: Close to N78B. Fully opened, upper and lower surfaces: Close to N74B; color does not change with development.

*Sepals*.—Arrangement: Typically five sepals in a single whorl; calyx roughly ovoid in shape. Length: About 4 mm. Width: About 2 mm. Shape: Ovate. Apex: Acute to rounded. Base: Cuneate. Margin: Entire. Texture and luster, upper and lower surfaces: Smooth, glabrous; matte. Color: When opening, upper and lower surfaces: Close to 60B. Fully opened, upper and lower surfaces: Close to 60D.

*Pedicels*.—Length: About 1 cm. Diameter: About 0.5 mm. Aspect: About 30° from the stem axis. Strength: Moderately strong. Texture and luster: Smooth, glabrous; matte. Color: Close to 71B.

*Reproductive organs*.—Androecium: Stamen number: About ten per flower. Filament length: About 1 mm. Filament color: Close to 69D. Anther shape: Oblong. Anther length: About 0.5 mm. Anther color: Close to 18C. Amount of pollen: Moderate. Pollen color: Close to 161B. Gynoecium: Pistil number: One per flower. Pistil length: About 1 cm. Style length: About 7.5 mm. Style color: Close to 71C. Stigma diameter: About 0.5 mm. Stigma shape: Rounded. Stigma color: Close to 145C. Ovary color: Close to 137B.

*Seeds and fruits*.—Seed and fruit development have not been observed on plants of the new *Cercis* to date.

Garden performance: Plants of the new *Cercis* have been observed to have good garden performance and to tolerate wind, rain and temperatures ranging from about −23.3° C. to about 37.7° C. and to be suitable for USDA Hardiness Zones 5 to 8.

Pathogen & pest resistance: Plants of the new *Cercis* have not been observed to be resistant to pathogens and pests common to *Cercis* plants.

It is claimed:

1. A new and distinct *Cercis* plant named 'JN16' as illustrated and described.

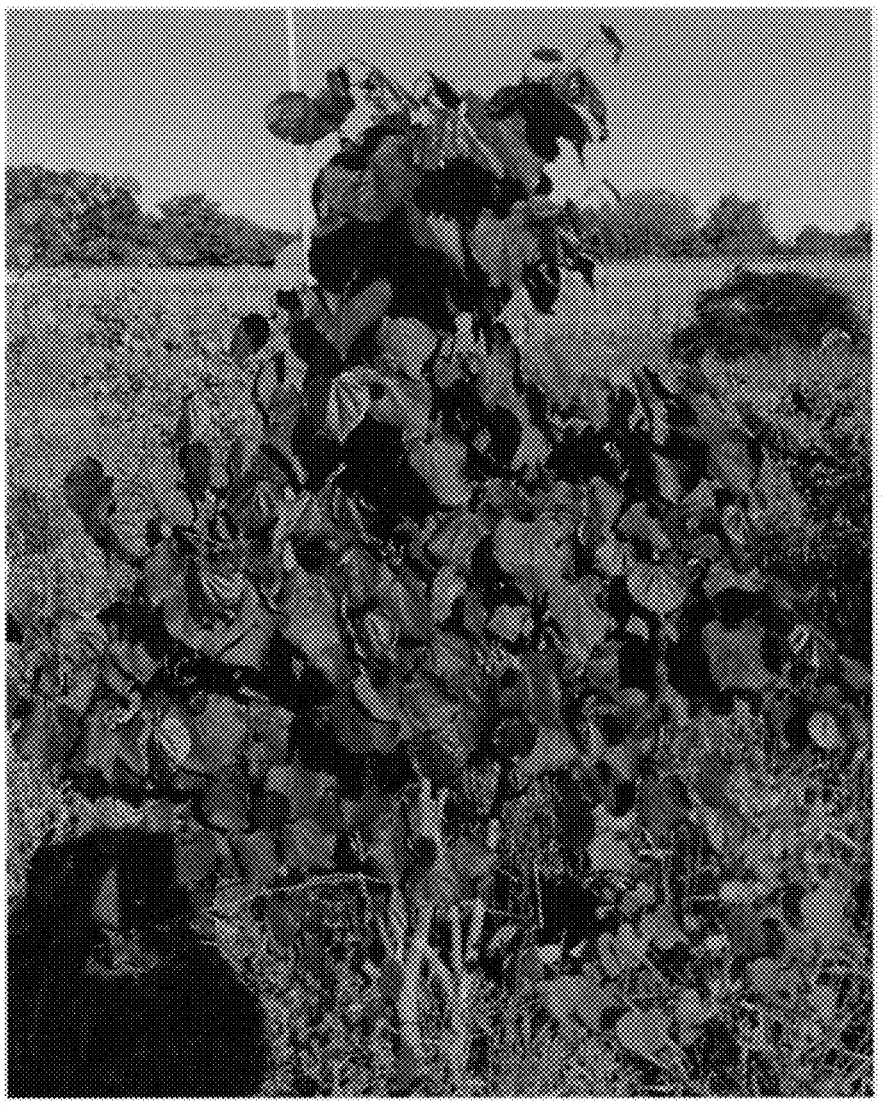

* * * * *